_US005938438A_

United States Patent [19]
Chipman et al.

[11] Patent Number: 5,938,438
[45] Date of Patent: Aug. 17, 1999

[54] DENTAL COMPOUND APPLICATOR

[75] Inventors: D. Keith Chipman, Genevieve; Roy Grantham, O'Fallon, both of Mo.

[73] Assignee: Young Dental Manufacturing Company, Earth City, Mo.

[21] Appl. No.: 09/074,986

[22] Filed: May 8, 1998

[51] Int. Cl.[6] ................................................. A61G 17/02
[52] U.S. Cl. ................................................ 433/80; 604/1
[58] Field of Search ................... 433/80; 604/1; 401/23, 24

[56] References Cited

U.S. PATENT DOCUMENTS

| D. 329,142 | 9/1992 | Discko, Jr. et al. | D4/104 |
|---|---|---|---|
| 532,720 | 1/1895 | Dennis | 433/164 |
| 532,721 | 1/1895 | Dennis | 433/164 |
| 1,410,311 | 3/1922 | Howe | 433/40 |
| 1,435,902 | 11/1922 | Derbyshire | 433/164 |
| 1,516,933 | 11/1924 | Terranova | 433/87 |
| 1,517,186 | 11/1924 | Bond | 433/116 |
| 2,294,186 | 8/1942 | Kirschbaum | 604/1 |
| 2,671,269 | 3/1954 | Francis | 433/116 |
| 3,018,778 | 1/1962 | Brilliant | 433/141 |
| 3,221,409 | 12/1965 | Thiel et al. | 433/83 |
| 3,611,469 | 10/1971 | Belli | 15/118 |
| 4,175,439 | 11/1979 | Laker | 604/1 |
| 4,424,036 | 1/1984 | Lokken | 433/116 |
| 4,752,223 | 6/1988 | Carlson | 433/116 |
| 4,973,248 | 11/1990 | Sigler | 433/90 |
| 5,001,803 | 3/1991 | Discko, Jr. | 15/167.1 |
| 5,098,297 | 3/1992 | Chari et al. | 433/80 |
| 5,150,495 | 9/1992 | Discko, Jr. et al. | 15/167.1 |
| 5,197,876 | 3/1993 | Coston | 433/116 |
| 5,647,746 | 7/1997 | Chipman | 433/226 |

*Primary Examiner*—John J. Wilson
*Attorney, Agent, or Firm*—Polster, Lieder, Woodruff & Lucchesi

[57] ABSTRACT

A dental applicator of the present invention is provided for applying a dental compound to a tooth surface. The applicator includes an applicator body having a handle and a neck extending forwardly from the handle. The neck has a forwardly facing socket or socket is formed at the end of the neck to receive an absorbent sponge. The sponge is slidingly received in the socket so that its position in the socket can be selectively changed. The sponge, when prepared for insertion into the socket, has an overall cross-sectional dimension greater than the diameter of the socket. The sponge thus has to be compressed when it is inserted in the socket. Thus, when the sponge is inserted in the socket, the sponge forms an enlarged, ball-shaped or bulbous tip. By selectively altering the amount the sponge extends from the end of the neck, the enlarged sponge tip can be made larger or smaller, to hold larger or smaller amounts of liquid.

13 Claims, 1 Drawing Sheet

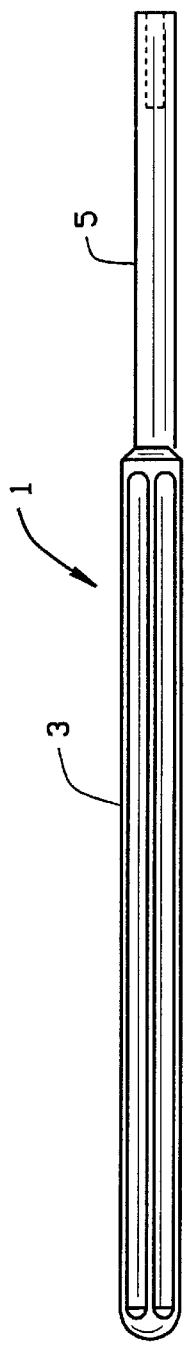
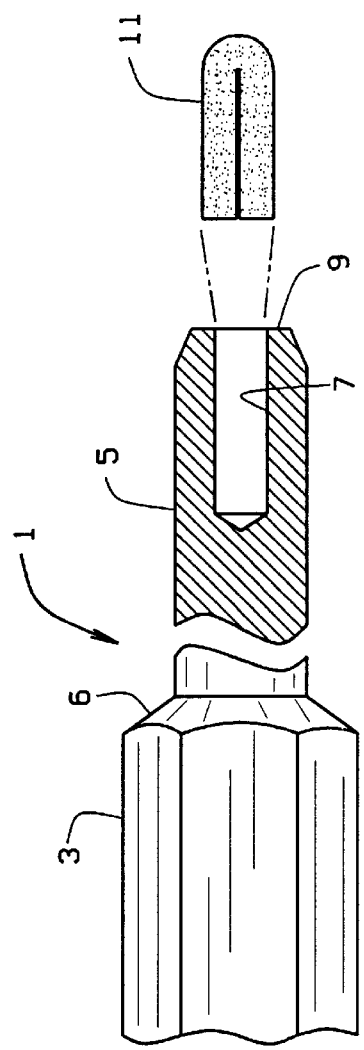
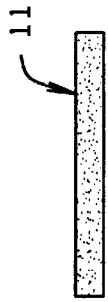
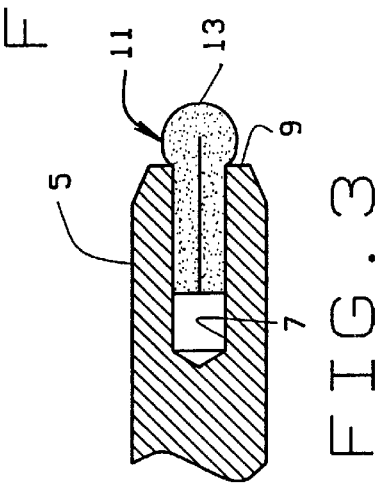

DENTAL COMPOUND APPLICATOR

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to applicators for applying dental compounds to patient's teeth, and, in particular, to a sponge tipped applicator which can be used to apply etchants, sealants, primers, adhesives, and other compounds to teeth to facilitate in the treatment of the teeth.

Dental compounds are typically applied to the tooth by an applicator. Numerous types of applicators have been designed. One such applicator is shown in U.S. Pat. No. 5,647,746, which is incorporated herein by reference. This applicator includes a shielded absorbent pad which is used to apply sealant to teeth. This applicator works well, but does not allow for easy control of the amount of sealant absorbed by the pad. A brush applicator is shown in U.S. Pat. No. 5,150,495. This brush applicator is commercially available from Centrix, Inc. under the name "Benda-Brush." Other applicators have a pick end with a tuft of absorbent material at the end of the pick. It is difficult to control the amount of compound absorbed by, or loaded onto, the applicator. Further, it is difficult to control the release of the compound from the applicators to the teeth. Thus, where a practitioner may want to apply only a small amount of compound to a tooth, or to only a selected part of a tooth, using the prior applicators, he may inadvertently apply compound to the whole tooth, or otherwise apply more compound than desired to the tooth.

BRIEF SUMMARY OF THE INVENTION

Briefly stated, a dental practitioner, such as a dentist, hygienist, technician, etc. can use a dental applicator of the present invention to apply a dental compound to a tooth surface during a dental procedure. The applicator includes a plastic disposable applicator body having a handle and a neck extending forwardly from the handle. The neck has a forwardly facing socket or opening formed at the end of the neck to receive an absorbent sponge. The neck is preferably thinner than the handle in diameter. The narrow diameter of the neck allows the dentist to selectively bend the neck of the applicator to allow the practitioner to reach hard to reach spots in the patient's mouth.

The sponge is not fixed in the socket. Rather, it is slidingly received in the socket so that its position in the socket can be selectively changed by the practitioner. The sponge, when prepared for insertion into the socket, has a cross-sectional dimension larger than the diameter of the socket. The sponge thus has to be compressed when it is inserted in the socket. The compression of the sponge causes the sponge to form an enlarged tip when it is inserted in the socket. Preferably, the sponge is folded in half prior to being inserted into the socket. When folded in half like this, the exposed tip of the sponge becomes rounded or bulbous. Because the sponge is not fixed in place in the socket, it can be moved relative to the socket, to vary the amount of sponge which extends from the socket. By selectively altering the amount the sponge extends from the end of the neck, the tip can be made larger or smaller, to hold greater or lesser amounts of liquid.

BRIEF DESCRIPTION OF THE SEVERAL VIEWS OF THE DRAWINGS

FIG. 1 is a plan view of an applicator handle of the present invention;

FIG. 2 is an enlarged exploded cross-sectional view of the applicator handle and a sponge tip;

FIG. 3 is an enlarged cross-sectional view of the end of the applicator handle with the sponge tip inserted therein; and FIG. 4 is a plan view of the sponge which is inserted into the end of the applicator.

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention.

An applicator 1 of the present invention includes a handle 3 which is graspable by a practitioner, and a neck 5 extending from the end of the handle 3. The applicator is preferably made of plastic, so that it can be easily molded and be of low cost to allow it to be disposed of after a single use. The handle 3 is preferably polygonal (hexagonal) in cross-section, but may be made any desired shape. The neck 5 is narrower in diameter than the handle 3, and the applicator 1 has a sloped transitional surface 6 between the handle 3 and the neck 5. The neck 5 is generally cylindrical and of a generally constant diameter. Preferably, the neck is about 0.1" in diameter. The plastic from which the handle is made is of a type that can be easily bent, and which will hold the deformation given to it. The use of such a plastic and the small diameter of the neck 5 allows for the neck 5 to be bent to a desired shape and to retain and to retain that shape during a dental procedure. The practitioner can thus bend the neck to enable him to more easily reach hard-to-reach places in a patient's mouth. A socket 7 extends axially rearwardly from the neck's forward end 9. The socket 7 defines a forwardly opening chamber. The socket 7 receives an absorbent foam element 11, such as a sponge, such that at least a portion of the absorbent foam element is enclosed by the socket.

The sponge 11 is preferably an elongate sponge, such as the rectangular sponge shown in FIG. 4, and is about 0.125"×1" in dimension. As seen in FIG. 2, the sponge 11 is folded over upon itself for insertion into the socket 7. When inserted into the socket 7, the sponge 11 protrudes from the end of the neck 5, as seen in FIG. 3, to be dipped into a compound, such as a fluoride solution, so that the compound can be applied to a patient's teeth. The diameter or cross-sectional dimension of the sponge 11, when folded in half, as seen in FIGS. 2 and 3, is greater than the diameter of the socket 7. Preferably, the socket has a diameter of about 0.05" to 0.06" and the largest cross-sectional dimension of the sponge 11, when folded in half for insertion in the socket, is about 0.125". Thus, the sponge 11 must be compressed to be inserted in the socket 7. The compression of the sponge 11 in the socket 7 causes the exposed portion of the sponge to form an enlarged tip 13. Because the sponge is preferably folded in half, the tip 13 which is formed is bulbous or ball-type in shape.

The tight fit of the sponge 11 in the socket 7 precludes the need to glue or otherwise fix the sponge in position in the socket 7. The sponge 11 is held in position in the socket 7 by frictional contact between the sponge 11 and the walls of the socket 7. Because the sponge is not positionally fixed in the socket 7, the sponge 11 can be slid axially with respect to the socket to selectively alter the amount of the sponge 11 which protrudes from the end of the applicator neck 5. When the amount of sponge extending from the end of the neck 5 is changed, the size of the enlarged tip 13 is also changed. The tip 13 becomes smaller as the sponge 11 is inserted farther into the socket 7. Conversely, the tip 13 increases in size as more of the sponge is exposed. When the amount of the sponge 11 protruding from the neck 5 is altered, and the size of the tip 13 is altered, the amount of compound which can be absorbed by the sponge, or loaded onto the sponge, for application to the teeth is also altered. The further the sponge protrudes from the neck, the more compound will be absorbed by, or loaded onto, the sponge for application to the teeth. Thus, for example, if the practitioner will be applying the compound to the tops of the teeth and to the sides of the teeth, he may want more of the sponge protruding, so that greater amounts of compound can be easily applied to the teeth. On the other hand, when the compound is applied to the teeth near the gums, the practitioner may want less of the sponge exposed, to prevent the solution from seeping or dripping down into the gingival margin, and to give him more control as to the application of the solution to the teeth.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense. Although the sponge 11 is preferably folded in half, as shown in FIG. 2, the sponge could be made shorter, and inserted in the applicator neck without being folded in half. However, by folding the sponge in half, as seen in FIG. 2, the applicator tip becomes rounded or curved which can facilitate application of solutions to teeth. The neck need not be of constant diameter. Rather, the neck could have a head at its end, and the socket 7 would be formed in the head. These examples are merely illustrative.

We claim:

1. A dental applicator for applying a compound to a tooth surface of a patient during a dental procedure; the applicator including an applicator body and an absorbent foam element; the applicator body including an axially extending, forwardly opening socket at an end of said body; the socket defining a chamber; the absorbent foam element being axially and slidably received in the socket; the absorbent foam element being enclosed by the socket with a portion of the foam element extending from the socket to be exposed; the amount of the foam element which is exposed being selectively alterable by a user of the applicator by selectively altering the degree to which the foam element is received in the socket.

2. The dental applicator of claim 1 wherein the portion of the foam element extending from the socket defines an enlarged tip.

3. The dental applicator of claim 1 wherein the foam element, when prepared for insertion in the socket, has an overall cross-sectional dimension greater than the diameter of the socket.

4. A dental applicator for applying a compound to a tooth surface of a patient during a dental procedure; the applicator including an applicator body having a handle, a neck extending forwardly from the handle, and an absorbent foam element received in a forward end of the neck; the neck including a socket at its end which slidably receives the foam element; the socket defining a chamber in which the foam element is received; the socket enclosing the foam element, the foam element being sized such that a portion of the foam element extends from the socket to be exposed; the exposed portion of the foam element extending forwardly from the end of the neck; the exposed portion of the foam element defining an enlarged, generally ball-shaped tip; the foam element, when prepared for insertion in the socket, having an overall cross-sectional dimension greater than the diameter of the socket.

5. The dental applicator of claim 4 wherein the foam element is a sponge.

6. A dental applicator for applying a compound to a tooth surface of a patient during a dental procedure; the applicator including an applicator body having a handle, a neck extending forwardly from the handle, and an absorbent foam element received in a forward end of the neck; the neck including a socket at its end which slidably receives the foam element; the socket enclosing the foam element, a portion of the foam element extends from the socket to be exposed; the exposed portion of the foam element extending forwardly from the end of the neck; the exposed portion of the foam element defining an enlarged tip; the foam element, when prepared for insertion in the socket, having an overall cross-sectional dimension greater than the diameter of the socket; the foam element being selectively movable in the socket relative to the neck to selectively alter the amount of the foam element that is exposed.

7. The dental applicator of claim 6 wherein the foam element is shaped to alter the size of the enlarged tip as the position of the sponge relative to the neck is selectively changed.

8. The dental applicator of claim 7 wherein the foam element, prior to being inserted in the socket, is generally oblong in shape, the foam element being folded over upon itself prior to insertion of the foam element in the socket.

9. A dental applicator for applying a compound to a tooth surface of a patient during a dental procedure; the applicator including an applicator body having a handle, a neck extending forwardly from the handle, a rearwardly extending socket defining a forwardly opening chamber in a forward end of the neck; and an absorbent foam element slidingly received in the socket to be at least partially enclosed by the socket; a portion of the foam element extending forwardly from the end of the neck to be exposed; the foam element, when prepared for insertion in the socket, having an overall cross-sectional dimension greater than the diameter of the socket; whereby when the foam element is inserted in the applicator body, the foam element defines an enlarged tip of the applicator, the amount of the absorbent foam element which is exposed being selectively alterable by axial movement of the foam element in the socket relative to the neck.

10. The dental applicator of claim 9 wherein the neck is narrower in diameter than the handle.

11. The dental applicator of claim 10 wherein the neck is bendable to a desired shape.

12. A dental applicator for applying a compound to a tooth surface of a patient during a dental procedure; the applicator including an applicator body having a handle,
a neck extending forwardly from the handle, the neck being narrower in diameter than the handle and bendable to a desired shape, the neck being made of a material which will maintain the desired shape when bent to the desired shape;

a rearwardly extending socket in a forward end of the neck; and an absorbent foam element slidingly received in the socket; the foam element extending forwardly from the end of the neck to be at least partially exposed; the foam element, when prepared for insertion in the socket, having an overall cross-sectional dimension greater than the diameter of the socket whereby when the foam element is inserted in the applicator body, the foam element defines an enlarged tip of the applicator, the size of the enlarged tip being selectively alterable by axial movement of the foam element in the socket relative to neck.

13. The dental applicator of claim 12 wherein the neck is made of plastic.

* * * * *